(12) United States Patent
Liang et al.

(10) Patent No.: US 11,874,219 B2
(45) Date of Patent: Jan. 16, 2024

(54) IN-SITU DETECTION DEVICE FOR DETECTING WATER AND FERTILIZER CONTENT IN CROP CULTIVATION SUBSTRATE AND DETECTION METHOD THEREOF

(71) Applicants: Qingdao Agricultural University, Qingdao (CN); Shandong Huijinhai Wisdom Agricultural Research Institute Co., Ltd., Weifang (CN); Weifang Huijinhai Internet of Things Technology Co., Ltd., Weifang (CN)

(72) Inventors: Bin Liang, Qingdao (CN); Baogang Xu, Weifang (CN); Lianfa Xu, Weifang (CN)

(73) Assignees: Qingdao Agricultural University, Qingdao (CN); Shandong Huijinhai Wisdom Agricultural Research Institute Co., Ltd., Weifang (CN); Weifang Huijinhai Internet of Things Technology Co., Ltd., Weifang (CN)

( * ) Notice: Subject to any disclaimer, the term of this patent is extended or adjusted under 35 U.S.C. 154(b) by 201 days.

(21) Appl. No.: 17/452,989

(22) Filed: Oct. 30, 2021

(65) Prior Publication Data

US 2022/0136958 A1    May 5, 2022

(30) Foreign Application Priority Data

Nov. 3, 2020   (CN) ......................... 202011206422.6

(51) Int. Cl.
*G01N 21/25*   (2006.01)
*G01F 23/30*   (2006.01)
(Continued)

(52) U.S. Cl.
CPC ............. *G01N 21/25* (2013.01); *G01F 23/30* (2013.01); *G01N 1/14* (2013.01); *G01N 21/01* (2013.01);
(Continued)

(58) Field of Classification Search
CPC .......... G01N 21/25; G01N 1/14; G01N 21/01; G01N 33/24; G01F 23/30
See application file for complete search history.

(56) References Cited

U.S. PATENT DOCUMENTS

2013/0301051 A1* 11/2013 Pogosyan .......... G01N 21/4738
250/578.1

FOREIGN PATENT DOCUMENTS

| CN | 205374442 U | * | 7/2016 | |
| CN | 109283017 A | * | 1/2019 | .............. G01N 1/10 |
| JP | 6285661 B2 | * | 2/2018 | |

\* cited by examiner

*Primary Examiner* — Uzma Alam
*Assistant Examiner* — Huy Phillip Pham
(74) *Attorney, Agent, or Firm* — Matthew J Patterson

(57) ABSTRACT

An in-situ detection device for detecting water and fertilizer content in a crop cultivation substrate and a detection method thereof are provided. The in-situ detection device includes a water and fertilizer in-situ collector and a spectrum analysis device. The water and fertilizer in-situ collector that is pre-buried in the cultivation substrate is used to collect water and fertilizer in the cultivation substrate in real time to obtain a measurement sample. The spectral analysis device is used to emit a laser with a specific wavelength to detect and analyze content of nitrogen, phosphorus, and potassium in the measurement sample collected by the water and fertilizer in-situ collector; and a continuous sampling system for continuously transporting the measurement sample is provided between the water and fertilizer in-situ collector and the spectrum analysis device.

3 Claims, 4 Drawing Sheets

(51) Int. Cl.
*G01N 1/14* (2006.01)
*G01N 21/01* (2006.01)
*G01N 33/24* (2006.01)
(52) U.S. Cl.
CPC ....... *G01N 33/24* (2013.01); *G01N 2033/245* (2013.01); *G01N 2201/0633* (2013.01); *G01N 2201/06113* (2013.01)

IN-SITU DETECTION DEVICE FOR DETECTING WATER AND FERTILIZER CONTENT IN CROP CULTIVATION SUBSTRATE AND DETECTION METHOD THEREOF

CROSS REFERENCE TO RELATED APPLICATION

This patent application claims the benefit and priority of Chinese Patent Application No. 202011206422.6 filed on Nov. 3, 2020, the disclosure of which is incorporated by reference herein in its entirety as part of the present application.

TECHNICAL FIELD

The present disclosure relates to the technical field of detection of nutrients in soil, in particular to an in-situ detection device for detecting water and fertilizer content in a crop cultivation substrate and a detection method thereof.

BACKGROUND ART

In the prior art, in order to increase the concentrations of nutrients in the crop cultivation substrate, water and fertilizer in liquid form is used as the cultivation substrate for irrigating the crops, thereby increasing the concentrations of nutrients in the cultivation substrate.

The nutrients in the cultivation substrate are present in the gaps of the cultivation substrate or in the water of the cultivation substrate, and are distributed in the soil that is from the ground surface down to the phreatic water table level. The nutrients are an important material component of the cultivation substrate and are also an important material basis for growth and development of crops.

The concentration of fertilizer in the water of the cultivation substrate is an important part of the research on the plant nutrition, and is also a research hotspot in terms of the safety of agricultural products and environmental risk prediction. In order to accurately irrigate the cultivation substrate by using water and fertilizer in liquid form, it is necessary to accurately detect the concentration of the fertilizer in the cultivation substrate.

In the prior art, when the nutrient concentration in the cultivation substrate is detected, the detection work is completed in the laboratory. First, the cultivation substrate is collected, and then the collected cultivation substrate is transported to the laboratory for detecting. The detection is complicated and the cultivation substrate is inconvenient to use, which cannot meet requirements for quickly obtaining the nutrition information of the farmland crop.

In order to solve the above technical problems, a soil nutrient detection system and a method occur on the market. For example, in the patent No. CN201510984791.0, a portable soil nutrient detection system and a method are disclosed. The micro sample chamber provides a closed space and air pressure environment during the detection process, and optically connects with the laser light path and the spectrum collection light path through the optical window. The laser device emits the laser. The spectrum collection and conversion module collects the optical signal in the plasma state that is generated when the soil to be tested is irradiated by the laser. The characteristic spectrum signal is generated via the spectrum collection and conversion module according to the optical signal, and the characteristic spectrum signal is converted into a digital signal via the spectrum collection and conversion module. According to the digital signal, a signal processing module obtains the spectral intensity signals corresponding to various elements in the to-be-measured soil. Based on the spectral intensity signals, the signal processing module calculates the content of various elements in the to-be-measured soil.

The above-mentioned soil nutrient detection system can detect the nutrients in the soil, whereas the detection requires manual assistance, which cannot realize automatic detection, and is inconvenient to use. In addition, the soil nutrient detection system is required to detect the soil, so the soil is pretreated when the soil is detected, thereby resulting in large deviations in the detection data, and in turn leading to inaccurate collection data.

In addition, the structure of the spectrum analysis device of the existing soil nutrient detection system is complicated, which causes the high costs for the manufacture and the usage. Furthermore, the wavelength of the light beam changes greatly, which affects detection data and causes the detection data to be inaccurate.

SUMMARY

The main technical problem to be solved by the present disclosure is to provide an in-situ detection device for detecting water and fertilizer content in a crop cultivation substrate having a simple structure and the convenience of use. The in-situ detection device can perform in-situ collection and analyzation on the water and fertilizer in liquid form in the crop cultivation substrate, and can accurately reflect the content of nutrients such as nitrogen, phosphorus and potassium in the crop cultivation substrate.

In order to solve the above technical problems, the present disclosure provides the following technical solutions.

An in-situ detection device for detecting water and fertilizer content in a crop cultivation substrate, wherein the in-situ detection device comprises a water and fertilizer in-situ collector and a spectral analysis device; the water and fertilizer in-situ collector is pre-buried in the crop cultivation substrate and used to collect water and fertilizer in the crop cultivation substrate in real time to obtain a measurement sample; the spectral analysis device is used to emit a laser with a specific wavelength to detect and analyze content of nitrogen, phosphorus, and potassium in the measurement sample collected by the water and fertilizer in-situ collector; and a continuous sampling system for continuously transporting the measurement sample is provided between the water and fertilizer in-situ collector and the spectrum analysis device.

The further optimization of the above technical scheme of the present disclosure is as follows.

The water and fertilizer in-situ collector comprises a water and fertilizer collection box and a water and fertilizer storage box; a communicating pipe is provided between the water and fertilizer collection box and the water and fertilizer storage box; the water and fertilizer collection box is used to collect water and fertilizer in the crop cultivation substrate in real time, to obtain the measurement sample; and the measurement sample is transported into the water and fertilizer storage box through the communicating pipe.

Preferably, a top collection port of the water and fertilizer collection box is provided with a filtration and permeation layer for filtering soil of the crop cultivation substrate; and a float liquid-level-detection switch is arranged in the water and fertilizer storage box.

Preferably, the spectrum analysis device comprises a laser light source; the laser light source is connected with a multi-mode laser splitter by a quartz fiber; the multi-mode laser splitter is installed with two light source circuits; and the two light source circuits comprise a measurement reference light-source-circuit and a measurement sample light-source-circuit.

Preferably, the multi-mode laser splitter splits laser emitted by the laser light source into a measurement reference laser-beam and a measurement sample laser-beam; the measurement reference laser-beam is transmitted along the measurement reference light-source-circuit; and the measurement sample laser-beam is transmitted along the measurement sample light-source-circuit.

Preferably, the measurement reference light-source circuit comprises a first collimator lens; a reference photodetector is arranged at a side of the first collimator lens, and the reference photodetector and the first collimator lens are spaced apart; and a reference transmittance cuvette is arranged between and spaced apart from the first collimator lens and the reference photodetector.

Preferably, the measurement sample light-source-circuit comprises a second collimator lens; a sample photodetector is arranged at a side of the second collimator lens, and the sample photodetector and the second collimator lens are spaced apart; and a sample transmittance cuvette is arranged between and spaced apart from the second collimator lens and the sample photodetector.

Preferably, the continuous sampling system comprises a first peristaltic pump and a second peristaltic pump; a liquid inlet end of the first peristaltic pump is communicated with the water and fertilizer storage box, and a liquid outlet end of the first peristaltic pump is communicated with a liquid inlet of the sample transmittance cuvette; a liquid inlet end of the second peristaltic pump is communicated with a reference sample pool, and a liquid outlet end of the second peristaltic pump is communicated with a liquid inlet of the reference transmittance cuvette.

The present disclosure adopts above-mentioned technical scheme, has ingenious concept and a reasonable structure, as well as can collect water and fertilizer in the cultivation substrate. Furthermore, the collection operation is convenient, the collection data is accurate, and the content of nitrogen, phosphorus, potassium and other nutrients in the collected water and fertilizer can be analyzed and detected in situ. So, the concentration of each nutrient in the soil cultivation substrate can be intuitively reflected. In addition, the detection data is accurate, which can ensure that the growth environment of crops is detected in real time, ensure the safety of the growth environment of agricultural products, and facilitate the risk prediction and analysis of the growth environment in real time. The overall structure is also stable, and no other refracting mirrors are required for light splitting, so that the overall structure of the device is simple and convenient to use.

The present disclosure also discloses an in-situ detection method of detecting water and fertilizer content in a crop cultivation substrate, the in-situ detection method being carried out by the in-situ detection device for detecting water and fertilizer content in the crop cultivation substrate above mentioned, wherein the in-situ detection method includes the following steps.

In step S1, pre-burying the water and fertilizer in-situ collector in the crop cultivation substrate.

In step S2, penetrating the water and fertilizer in the crop cultivation substrate into a water and fertilizer collection box of the water and fertilizer in-situ collector through a filtration and permeation layer on the water and fertilizer collection box; and enabling the water and fertilizer to enter a water and fertilizer storage box of the water and fertilizer in-situ collector through a communicating pipe to obtain the measurement sample.

In step S3, enabling the continuous sampling system to continuously transport a reference sample and the measurement sample to a measurement reference light-source-circuit and a measurement sample light-source-circuit in a multi-mode laser splitter, respectively.

In step S4, enabling a laser light source of the spectrum analysis device to emit light with a specific wavelength and transmitting the light to the multi-mode laser splitter; enabling the multi-mode laser splitter to split the light into a measurement reference laser-beam and a measurement sample laser-beam; enabling the measurement reference laser-beam to be transmitted along the measurement reference light-source-circuit to a reference transmittance cuvette, so as to irradiate the reference sample; enabling the measurement sample laser-beam to be transmitted to a sample transmittance cuvette along the measurement sample light-source-circuit, so as to irradiate the measurement sample.

In step S5, enabling a reference photodetector of the measurement reference light-source circuit to detect absorbance when the measurement reference laser-beam irradiates the reference sample in the reference transmittance cuvette, so as to obtain reference absorbance.

In step S6, enabling a sample photodetector of the measurement sample light-source-circuit to detect absorbance when the measurement sample laser-beam irradiates the measurement sample in the sample transmittance cuvette, so as to obtain sample absorbance.

In step S7, obtaining signals of both the reference absorbance and the sample absorbance; obtaining actual sample absorbance, through a formula that the sample minus the reference absorbance is the actual sample absorbance; and calculating content of corresponding nutrient elements in the measurement sample according to the actual sample absorbance.

The further optimization of the above technical scheme of the present disclosure is as follows.

In step S4, the laser light source comprises a laser light source for detecting nitrogen, a laser light source for detecting phosphorus, and a laser light source for detecting potassium; a wavelength of the laser light source for detecting nitrogen is 217 nm; a wavelength of the laser light source for detecting phosphor is 490 nm; and a wavelength of the laser light source for detecting potassium is 440 nm.

The present disclosure adopts the above technical scheme and has ingenious concept. Water and fertilizer in the cultivation substrate is collected in real time to obtain a measurement sample, and then the online in-situ automatic analysis and detection on the measurement sample are performed. In this way, the content of nutrients such as nitrogen, phosphorus, potassium and the like in the cultivation substrate can be accurately detected, which is easy to use. Furthermore, the detection operation is to detect the water and fertilizer in the cultivation substrate. So, compared with the detection of the soil, the detection of the cultivation substrate is more convenient, and the detection data thereof is accurate, which can intuitively reflect the concentration of each nutrient in the crop cultivation substrate. Further, the safety of the growth environment of agricultural products is ensured, and the real-time risk prediction and analysis on this growth environment are also convenient.

The present disclosure will be further described below with reference to the drawings and embodiments.

Figure 1:
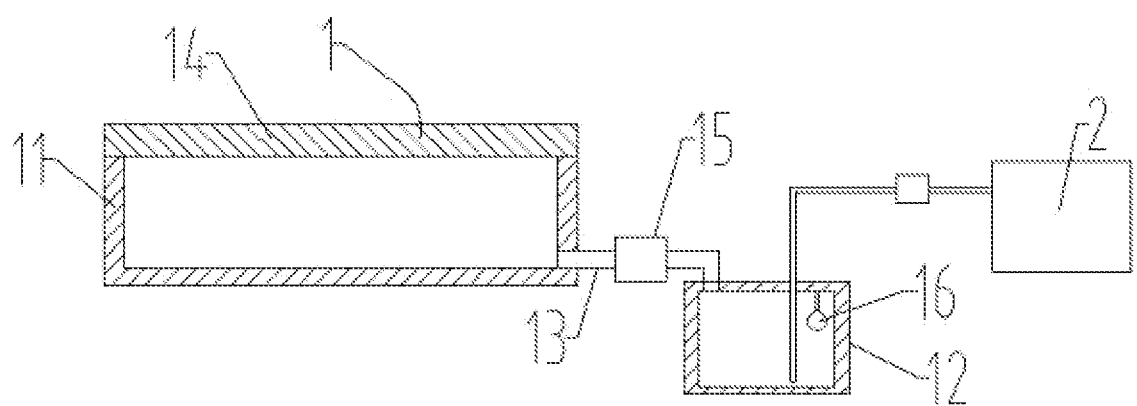
FIG. 1 is a schematic diagram of an overall structure according to an embodiment of the present disclosure.
Figure 2:
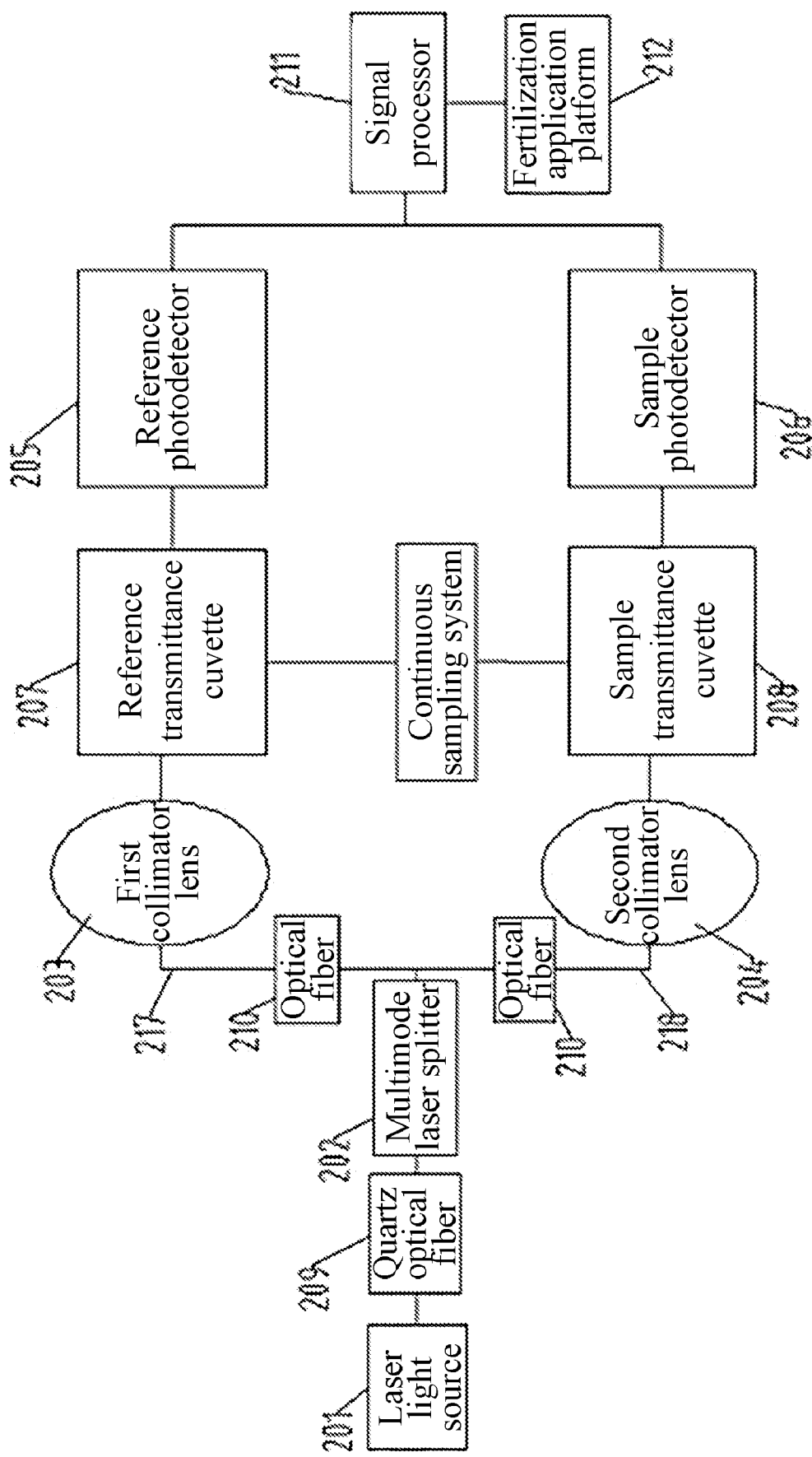
FIG. 2 is an overall schematic diagram of a spectrum analysis device according to an embodiment of the present disclosure.

Reference signs in the drawings: 1—water and fertilizer in-situ collector; 11—water and fertilizer collection box; 12—water and fertilizer storage box; 13—communicating pipe, 14—filtration and permeation layer; 15—filter; 16—float liquid-level-detection switch; 2—spectral analysis device; 201—laser light source; 202—multi-mode laser splitter; 203—first collimator lens; 204—second collimator lens; 205—reference photodetector; 206—sample photodetector; 207—reference transmittance cuvette; 208—sample transmittance cuvette; 209—quartz fiber; 210—fiber; 211—signal processor; 212—fertilization application platform; 213—first peristaltic pump; 214—second peristaltic pump; 215—liquid inlet pipe; 216—liquid outlet pipe; 217—measurement reference light-source-circuit; 218—measurement sample light-source-circuit; 219—reference sample pool; 3—cultivation substrate.

DETAILED DESCRIPTION OF THE EMBODIMENTS

In examples, as shown in FIGS. 1-6, an in-situ detection device for detecting water and fertilizer content in a crop cultivation substrate is provided. The in-situ detection device includes a water and fertilizer in-situ collector 1 and a spectral analysis device 2. The water and fertilizer in-situ collector 1 is pre-buried in the crop cultivation substrate 3 and used to collect water and fertilizer in the crop cultivation substrate 3 in real time to obtain a measurement sample. The spectral analysis device 2 is used to emit a laser with a specific wavelength to detect and analyze content of nitrogen, phosphorus, and potassium in the measurement sample collected by the water and fertilizer in-situ collector 1. A continuous sampling system for continuously transporting the measurement sample is provided between the water and fertilizer in-situ collector 1 and the spectrum analysis device 2.

Figure 6:
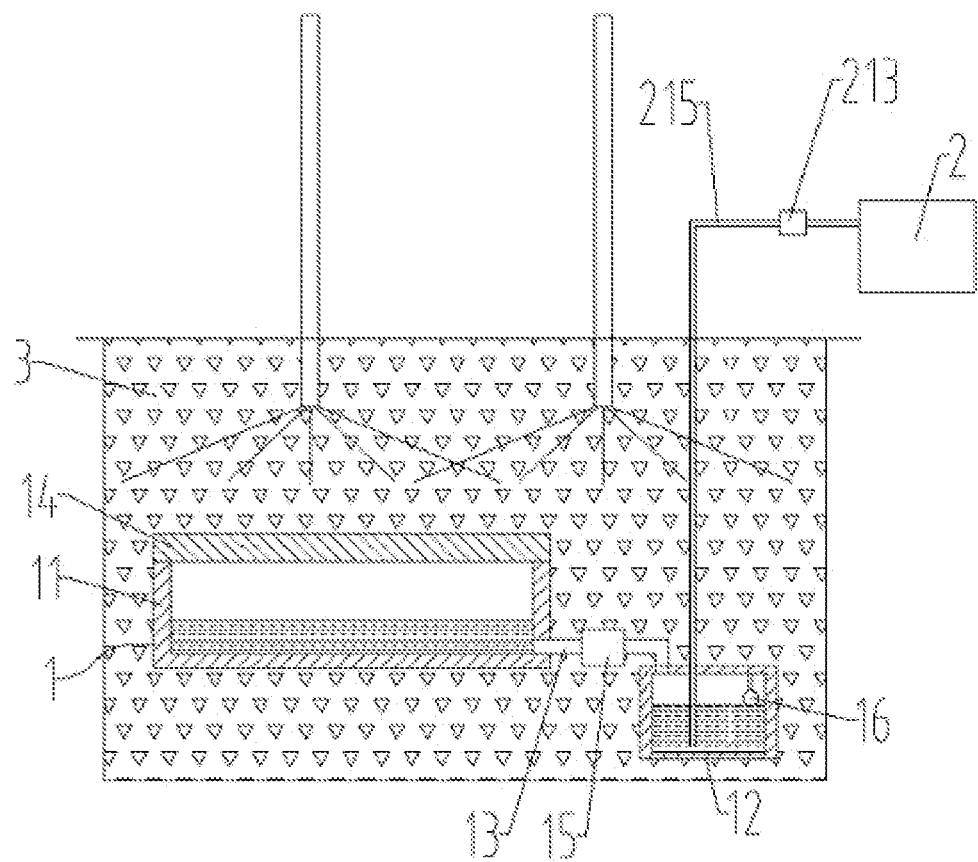
FIG. 6 is a schematic structural diagram showing an application scenario according to an embodiment of the present disclosure.

As shown in FIGS. 1 and 6, the water and fertilizer in-situ collector 1 includes a water and fertilizer collection box 11 and a water and fertilizer storage box 12. A communicating pipe 13 is provided between the water and fertilizer collection box 11 and the water and fertilizer storage box 12. The water and fertilizer collection box 11 and the water and fertilizer storage box 12 are pre-buried in the cultivation substrate 3 (i.e., the crop cultivation substrate). The water and fertilizer collection box 11 is used to collect water and fertilizer in soil of the crop cultivation substrate 3 in real time, to obtain the measurement sample. The measurement sample is transported into the water and fertilizer storage box 12 through the communicating pipe 13.

So, the water and fertilizer in the cultivation substrate 3 can penetrate into the water and fertilizer collection box 11 based on the permeation principle. At this time, the water and fertilizer collection box 11 is used to collect the water and fertilizer in the cultivation substrate 3 to obtain the measurement sample. Then, the water and fertilizer in the water and fertilizer collection box 11 is transported into the water and fertilizer storage box 12 through the communicating pipe 13.

When a level of the water and fertilizer in the water and fertilizer storage box 12 reaches the preset liquid level, the continuous sampling system may transport the measurement sample in the water and fertilizer storage box 12 to the spectral analysis device 2. The spectral analysis device 2 then may perform online analysis and detection on the measurement sample in real time to obtain the content of nitrogen, phosphorus, and potassium in the measured sample. In this way, the content of nitrogen, phosphorus, and potassium in the water and fertilizer of the cultivation substrate 3 are intuitively reflected, the detection data is accurate, and the real-time detection of the growth environment of crops is ensured, thereby enabling users to conveniently and accurately irrigate by using the water and fertilizer in liquid form according to the nutrient content of the water and fertilizer in the cultivation substrate 3. Furthermore, the safety of the growth environment of agricultural products is ensured, and the real-time risk prediction and analysis of the growth environment may be convenient.

The water and fertilizer collection box 11 is provided with a collection cavity. A top part of the water and fertilizer collection box 11 is provided with a collection port communicating with the collection cavity. A filtration and permeation layer 14 is provided at the collection port of the water and fertilizer collection box 11. Through the filtration and permeation layer 14, the soil of the soil cultivation substrate (i.e., the crop cultivation substrate) is filtered.

The filtration and permeation layer 14 is provided at the collection port of the water and fertilizer collection box 11. The filtration and permeation layer 14 can filter the silt of the cultivation substrate 3, and block the silt from the outside of the water and fertilizer collection box 11, thereby enabling only the water and fertilizer in the cultivation substrate 3 to penetrate into the water and fertilizer collection box 11 through the filtration and permeation layer 14, which can be convenient to use and improve the quality of the water and fertilizer collected.

The filtration and permeation layer 14 is a non-woven fabric layer, and the overall thickness of the filtration and permeation layer 14 is 40-80 mm.

The non-woven fabric layer has the air permeability and does not absorb water. So, the non-woven fabric layer is arranged at the collection port of the water and fertilizer collection box 11, so as to filter the silt of the cultivation substrate 3 and block the silt outside the water and fertilizer collection box 11, thereby only allowing the water and fertilizer in the cultivation substrate 3 to penetrate into the water and fertilizer collection box 11 through the non-woven fabric layer.

In the embodiment, the entire water and fertilizer collection box 11 and the water and fertilizer storage box 12 can be wholly made of plastic or stainless steel.

The overall structures of both the water and fertilizer collection box 11 and the water and fertilizer storage box 12 can be rectangular parallelepiped shapes, cube shapes, spherical shapes, and other geometric shapes.

A filter 15 for filtering the water and fertilizer in liquid form conveyed in the communicating pipe 13 is arranged in series on the communicating pipe 13. The filter 15 is arranged on the communicating pipe 13 between the water and fertilizer collection box 11 and the water and fertilizer storage box 12.

The water and fertilizer storage box 12 is provided with a float liquid-level-detection switch 16 for detecting the liquid level of the water and fertilizer stored in the water and fertilizer storage box 12.

The float liquid-level-detection switch 16 is arranged in the water and fertilizer storage box 12. The float liquid-level-detection switch 16 can detect a highest liquid level in the water and fertilizer storage box 12.

The float liquid-level-detection switch 16 acts along with the liquid level of the water and fertilizer in the water and fertilizer storage box 12. When the liquid level of the water and fertilizer in the water and fertilizer storage box 12 reaches the highest liquid level, the float liquid-level-detection switch 16 is activated, which represents that the liquid level of the water and fertilizer stored in the water and fertilizer storage box 12 has reached the highest liquid level.

When the liquid level of the water and fertilizer in the water and fertilizer storage box 12 reaches the highest liquid level, it means that the water and fertilizer in the water and fertilizer storage box 12 is sufficient to use to detect the concentration of the water and fertilizer one time, which is convenient for using.

As shown in FIGS. 2-5, the spectrum analysis equipment 2 includes a laser light source 201 connected to a multi-mode laser splitter 202 through a quartz fiber 209, and the multi-mode laser splitter 202 is installed with two light-source-circuits. The two light-source-circuits are a measurement reference light-source-circuit 217 and a measurement sample light-source-circuit 218.

The continuous sampling system transports the collected measurement sample in the water and fertilizer storage box 12 to the measurement sample light-source-circuit 218. The continuous sampling system can also continuously transport the reference sample to the measurement reference light-source-circuit 217.

The laser light source 201 can emit laser light with a specific wavelength. The laser light is transmitted to the multi-mode laser splitter 202 through the quartz fiber 209. The multi-mode laser splitter 202 splits the laser light with the specific wavelength emitted by the laser light source 201 to two laser light beams. The intensity of the laser light with the specific wavelength after being split becomes weaker, whereas the wavelength thereof may be not changed.

The quartz fiber 209 can be used to guide and transmit the laser light emitted by the laser light source 201, so as to facilitate the arrangement of the laser light source 201 and the multi-mode laser splitter 202, which is convenient to use.

The two laser light beams with specific wavelengths are split by the multi-mode laser splitter 202 are respectively the measurement reference laser-beam and the measurement sample laser-beam.

The measurement reference laser-beam is transmitted along the measurement reference light-source-circuit 217. The measurement reference laser-beam is used for detecting and analyzing the absorbance of the reference sample in the measurement reference light-source-circuit 217.

The measurement sample laser-beam is transmitted along the measurement sample light-source-circuit 218. The measurement sample laser-beam is used to detect and analyze the absorbance of the measurement sample in the measurement sample light-source-circuit 218, thereby detecting and analyzing the nutrient content in the sample.

The laser light source 201 is a laser emitting device having adjustable power. The power of the laser emitted by the laser light source 201 can be adjusted by adjusting the power of the laser emitting device.

The laser light source 201 is an existing technology and can be directly purchased on the market.

The measurement reference light-source-circuit 217 includes a first collimator 203. A reference photodetector 205 is arranged at a side of the first collimator lens 203, and the reference photodetector and the first collimator lens are spaced apart. A reference transmittance cuvette 207 is arranged between and spaced apart from the first collimator lens 203 and the reference photodetector 205.

The first collimator lens 203 and the reference photodetector 205 are arranged in parallel, and a beam focusing point of the first collimator lens 203 and a detection point of the reference photodetector 205 are located on a same straight line.

The first collimator lens 203 is used for condensing the measurement reference laser-beam transmitted in the measurement reference light-source-circuit 217 and adjusting the position of the measurement reference laser-beam.

The measurement sample light-source-circuit 218 includes a second collimator lens 204. A sample photodetector 206 is arranged at a side of the second collimator lens 204, and the sample photodetector and the second collimator lens are spaced apart. A sample transmittance cuvette 208 is arranged between and spaced apart from the second collimator lens 204 and the sample photodetector 206.

The second collimator lens 204 and the sample photodetector 206 are arranged in parallel, and a beam focusing point of the second collimator lens 204 and a detection point of the sample photodetector 206 are located on a same straight line.

The second collimator lens 204 is used for condensing the measurement sample laser-beam transmitted in the measurement sample light-source-circuit 218 and adjusting the position of the measurement sample laser-beam.

When the nutrient content in the sample needs to be measured, the continuous sampling system inputs the reference sample into the reference transmittance cuvette 207; and the continuous sampling system also inputs the measurement sample into the sample transmittance cuvette 208.

Then, the laser light emitted by the laser light source 201 is split into the measurement reference laser-beam and the measurement sample laser-beam by the multi-mode laser splitter 202. The measurement reference laser-beam is transmitted along the measurement reference light-source-circuit 217. At this time, the measurement reference laser-beam is gathered via the first collimator lens 203; then transmitted through the reference transmittance cuvette 207 containing the reference sample; and finally imaged on the detection point of the reference photodetector 205. So, the reference photodetector 205 is used to detect the absorbance, and further obtain reference absorbance.

Then, the measurement sample laser-beam is transmitted along the measurement sample light-source-circuit 218. At this time, the measurement sample laser-beam is gathered via the second collimator lens 204; and then transmitted through the sample transmittance cuvette 208 containing the measurement sample. At this time, the light of the measurement sample laser-beam that is transmitted through the sample transmittance cuvette 208 is absorbed by the atoms in the sample transmittance cuvette 208, and the measurement sample laser-beam is imaged on the detection point of the sample photodetector 206. So, the sample photodetector 206 may be used for detecting the absorbance of the measurement sample, and further obtaining the sample absorbance.

Furthermore, through the formula that the sample absorbance minus the reference absorbance is the actual sample absorbance, the actual sample absorbance can be obtained. The actual sample absorbance can be used to accurately calculate the nutrient content in the measurement sample to be measured.

Fibers 210 are arranged between the multi-mode laser splitter 202 and the first collimator 203, between the multi-mode laser splitter 202 and the second collimator lens 204, respectively. The measurement reference laser-beam and the measurement sample laser-beam are split by the multi-mode laser splitter 202, and are transmitted to the first collimator lens 203 and the second collimator lens 204 through respective fibers 210, respectively.

The fibers 210 are used to guide and transmit the measurement reference laser-beam and the measurement sample laser-beam split by the multi-mode laser splitter 202, thereby facilitating the transmission of the measurement reference laser-beam and the measurement sample laser-beam, which is convenient to use.

There are three laser light sources 201, and the three laser light sources 201 include a laser light source for detecting nitrogen, a laser light source for detecting phosphor, and a laser light source for detecting potassium.

The laser light source for detecting nitrogen is used to detect, analyze and determine the content of nitrogen in the sample; the absorption wavelength of the nitrogen is 210-230 nm; and the wavelength of the laser light source for detecting nitrogen is preferably 217 nm.

The laser light source for detecting phosphor is used to detect, analyze and determine the content of phosphorus in the sample; the absorption wavelength of the phosphorus is 460-490 nm; and the wavelength of the laser light source for detecting phosphor is preferably 490 nm.

The laser light source for detecting potassium is used to detect, analyze and determine the content of potassium in the sample; the absorption wavelength of the potassium is 420-450 nm; and the wavelength of the laser light source for detecting potassium is preferably 440 nm.

The output ends of both the reference photodetector 205 and the sample photodetector 206 are electrically connected with a signal processor 211. The signal processor 211 is used to process light intensity signals detected by both the reference photodetector 205 and the sample photodetector 206.

The signal processor 211 is an existing technology and is used for data processing and data transmission.

An output terminal of the signal processor 211 is electrically connected to a fertilizer application platform 212. The fertilizer application platform 212 is configured to receive a signal sent by the signal processor 211, and control the fertilizer application machine to perform fertilization according to the signal.

Figure 3:
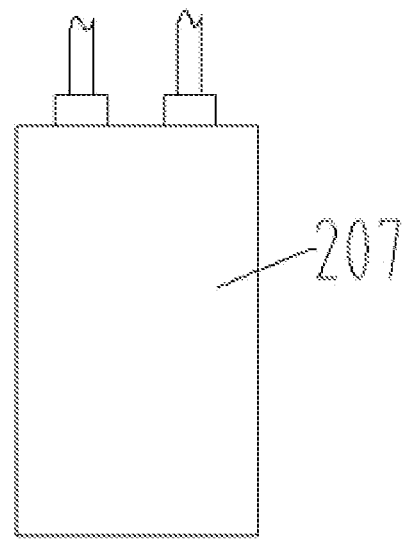
FIG. 3 is a schematic structural diagram of a reference transmittance cuvette according to an embodiment of the present disclosure.

As shown in FIG. 3, both the reference transmittance cuvette 207 and the sample transmittance cuvette 208 have the same overall shapes and specifications, and are both made of light-transmitting glass. The overall wall thicknesses of both the reference transmittance cuvette 207 and the sample transmission cuvette 208 are 2-5 mm.

The reference transmittance cuvette 207 and the sample transmittance cuvette 208 are provided with each a liquid storage cavity. Each of top portions of both the reference transmittance cuvette 207 and the sample transmittance cuvette 208 is provided with a liquid inlet and a liquid outlet which are communicated with the liquid storage cavity.

Figure 4:
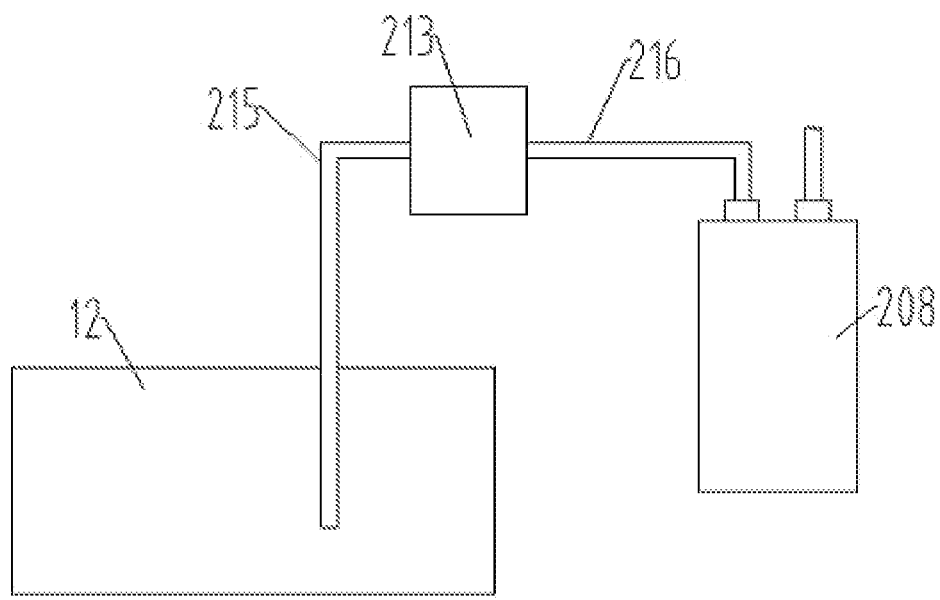
FIG. 4 is a schematic diagram of connecting relationship of a first peristaltic pump according to an embodiment of the present disclosure.
Figure 5:
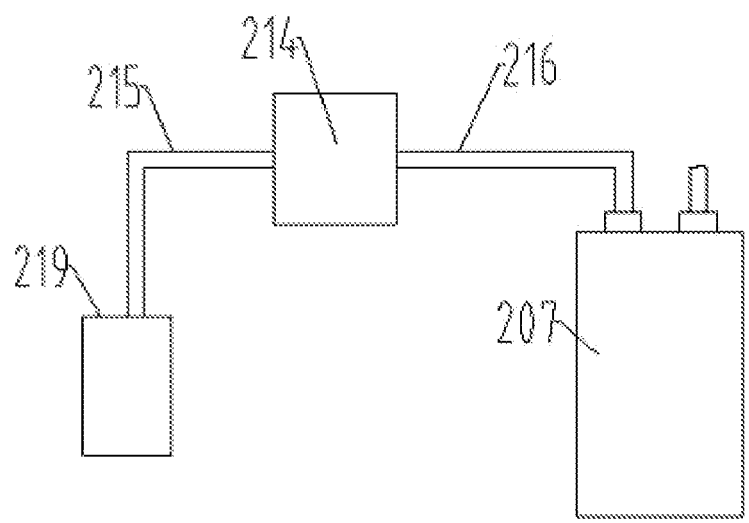
FIG. 5 is a schematic diagram of connecting relationship of a second peristaltic pump according to an embodiment of the present disclosure.

As shown in FIGS. 1 and 4-5, the continuous sampling system includes a first peristaltic pump 213 and a second peristaltic pump 214. A liquid inlet end and a liquid outlet end of the first peristaltic pump 213 are respectively connected with a liquid inlet pipe 215 and a liquid outlet pipe 216; and a liquid inlet end and a liquid outlet end of the second peristaltic pump 214 are also respectively connected with the liquid inlet pipe 215 and the liquid outlet pipe 216.

The liquid inlet end of the first peristaltic pump 213 communicates with the water and fertilizer storage box 12 through the liquid inlet pipe 215; and the liquid outlet end of the first peristaltic pump 213 communicates with the liquid inlet of the sample transmittance cuvette 208 through the liquid outlet pipe 216.

The liquid inlet end of the second peristaltic pump 214 communicates with the reference sample pool 219 through the liquid inlet pipe 215; and the liquid outlet end of the second peristaltic pump 214 communicates with the liquid inlet of the reference transmittance cuvette 207 through the liquid outlet pipe 216.

The reference sample is stored in the reference sample pool 219, and the reference sample is water.

The first peristaltic pump 213 can suck the collected measurement sample in the water and fertilizer storage box 12 through the liquid inlet pipe 215 and transport the measurement sample into the sample transmittance cuvette 208 through the liquid outlet pipe 216. At this time, the sample transmittance cuvette 208 is used to store the measurement sample.

The second peristaltic pump 214 can suck the reference sample in the reference sample pool 219 through the liquid inlet pipe 215, and transport the reference sample into the reference transmittance cuvette 207 through the liquid outlet pipe 216. At this time, the transmittance cuvette 207 is used to store the reference sample.

In addition, the first peristaltic pump 213 and the second peristaltic pump 214 can accurately calculate the measurement sample and the reference sample transported in the respective liquid inlet pipe 215 and the respective liquid outlet pipe 216, so that volumes of the liquid samples contained in both the reference transmittance cuvette 207 and the sample transmittance cuvette 208 are the same, which improves the accuracy of the detection data.

The liquid outlets of both the reference transmittance cuvette 207 and the sample transmittance cuvette 208 are in communication with a barrel for collecting waste water. So, the liquid samples after being detected in both the reference transmittance cuvette 207 and the sample transmittance cuvette 208 may be guided to the barrel for collecting waste water via the liquid port, so as to collect and treat the liquid samples.

As shown in FIGS. 1-6, the present disclosure also discloses an in-situ detection method for detecting water and fertilizer content in a crop cultivation substrate; and the in-situ detection method is carried out by the above-mentioned in-situ detection device for detecting water and fertilizer content in the crop cultivation substrate. The method includes the following steps S1 to S7.

In step S1, the water and fertilizer in-situ collector 1 is pre-buried in the cultivation substrate 3; and the water and fertilizer in-situ collector 1 is located directly below the root of the crop in the cultivation substrate 3, or at two sides of the root of the crop in the cultivation substrate 3.

In step S2, the water and fertilizer in the cultivation substrate 3 is penetrated into the water and fertilizer collection box 11 through the filtration and permeation layer 14; and the water and fertilizer is enabled to enter the water and fertilizer storage box 12 through the communicating pipe 13 to obtain the measurement sample in the cultivation substrate 3.

In step S3, the continuous sampling system is enabled to continuously transport the reference sample and the measurement sample to the measurement reference light-source-circuit 217 and the measurement sample light-source-circuit 218, respectively.

In the step S3, when the continuous sampling system continuously transports the reference sample and the measurement sample, the first peristaltic pump 213 and the second peristaltic pump 214 are operated. The first peristaltic pump 213 sucks the collected measurement sample in the water and fertilizer storage box 12 through the liquid inlet pipe 215, and transports the measurement sample into the sample transmittance cuvette 208 through the liquid outlet pipe 216.

The second peristaltic pump 214 sucks the reference sample in the reference sample pool 219 through the liquid inlet pipe 215, and transports the reference sample into the reference transmittance cuvette 207 through the liquid outlet pipe 216.

In step S4, the laser light source 201 is enabled to emit light with a specific wavelength and the light is transmitted to the multi-mode laser splitter 202; the multi-mode laser splitter 202 is enabled to split the light with the specific wavelength into the measurement reference laser-beam and the measurement sample laser-beam; the measurement reference laser-beam is enabled to be transmitted along the measurement reference light-source-circuit 217 to the reference transmittance cuvette 207, so as to irradiate the reference sample; the measurement sample laser-beam is enabled to be transmitted to a sample transmittance cuvette 208 along the measurement sample light-source-circuit 218, so as to irradiate the measurement sample.

In the step S4, the laser light source 201 includes three laser light sources 201. The three laser light sources 201 are a laser light source for detecting nitrogen, a laser light source for detecting phosphorus, and a laser light source for detecting potassium.

The laser light source for detecting nitrogen is used to detect, analyze and determine the content of nitrogen in the sample; the absorption wavelength of the nitrogen is 210-230 nm; and the wavelength of the laser light source for detecting nitrogen is preferably 217 nm.

The laser light source for detecting phosphor is used to detect, analyze and determine the content of phosphorus in the sample; the absorption wavelength of the phosphorus is 460-490 nm; and the wavelength of the laser light source for detecting phosphor is preferably 490 nm.

The laser light source for detecting potassium is used to detect, analyze and determine the content of potassium in the sample; the absorption wavelength of the potassium is 420-450 nm; and the wavelength of the laser light source for detecting potassium is preferably 440 nm.

In step S5, the reference photodetector 205 is enabled to detect absorbance when the measurement reference laser-beam irradiates the reference sample in the reference transmittance cuvette 207, so as to obtain reference absorbance; and the reference absorbance is transmitted to the signal processor 211.

In step S6, the sample photodetector 206 is enabled to detect absorbance when the measurement sample laser-beam irradiates the measurement sample in the sample transmittance cuvette 208, so as to obtain sample absorbance; and the sample absorbance is transmitted to the signal processor 211.

In step S7, signals of both the reference absorbance and the sample absorbance are obtained by the signal processor 211; actual sample absorbance is obtained, through a formula that the sample minus the reference absorbance is the actual sample absorbance; and content of corresponding nutrient elements in the measurement sample is calculated according to the actual sample absorbance.

It should be noted that, one laser light source 201 can only emit light of a single one specific wavelength, so that when the content of nitrogen, phosphorus, and potassium in the measurement sample needs to be detected, the laser light source for detecting nitrogen, the laser light source for detecting phosphorus, and the laser light source for detecting potassium are necessary to be selected, respectively.

In addition, the concentrations of nutrients such as nitrogen, phosphorus, and potassium in the cultivation substrate 3 are an important factor that affects the growth of crops. The cultivation substrate 3 also includes other trace elements, such as calcium, phosphorus, manganese, zinc, boron, and iron.

The in-situ detection method for detecting water and fertilizer content in the cultivation substrate 3 can also be used to detect the concentrations of trace elements such as calcium, phosphorus, manganese, zinc, boron, and iron in the cultivation substrate 3.

The detection of the concentrations of trace elements (such as calcium, phosphorus, manganese, zinc, boron and iron) is performed by different laser light sources 201 emitting lasers having different wavelengths. So, the wavelengths of the lasers emitted by the laser light sources 201 are selected and thus the concentrations of the nutrients in cultivation substrate 3 are detected.

For those of ordinary skill in the art, changes, modifications, substitutions and variations made to the embodiments based on the teachings of the present disclosure, without departing from the principle and spirit of the present disclosure still fall within the protection scope of the present disclosure.

What is claimed is:

1. An in-situ detection device for detecting water and fertilizer content in a crop cultivation substrate, wherein the in-situ detection device comprises a water and fertilizer in-situ collector and a spectral analysis device; the water and fertilizer in-situ collector is pre-buried in the crop cultivation substrate and used to collect water and fertilizer in the crop cultivation substrate in real time to obtain a measurement sample; the spectral analysis device is used to emit a laser with a specific wavelength to detect and analyze content of nitrogen, phosphorus, and potassium in the measurement sample collected by the water and fertilizer in-situ collector; and a continuous sampling system for continuously transporting the measurement sample is provided between the water and fertilizer in-situ collector and the spectrum analysis device;

wherein the water and fertilizer in-situ collector comprises a water and fertilizer collection box and a water and fertilizer storage box; a communicating pipe is provided between the water and fertilizer collection box and the water and fertilizer storage box; the water and fertilizer collection box is used to collect water and fertilizer in the crop cultivation substrate in real time, to obtain the measurement sample; and the measurement sample is transported into the water and fertilizer storage box through the communicating pipe;

wherein a top collection port of the water and fertilizer collection box is provided with a filtration and permeation layer for filtering soil of the crop cultivation substrate; and a float liquid-level-detection switch is arranged in the water and fertilizer storage box;

wherein the spectrum analysis device comprises a laser light source; the laser light source is connected with a multi-mode laser splitter by a quartz fiber; the multi-mode laser splitter is installed with two light source circuits; and the two light source circuits comprise a measurement reference light-source-circuit and a measurement sample light-source-circuit;

wherein the multi-mode laser splitter splits laser emitted by the laser light source into a measurement reference laser-beam and a measurement sample laser-beam; the measurement reference laser-beam is transmitted along the measurement reference light-source-circuit and the measurement sample laser-beam is transmitted along the measurement sample light-source-circuit;

wherein, the measurement reference light-source circuit comprises a first collimator lens; a reference photodetector is arranged at a side of the first collimator lens, and the reference photodetector and the first collimator lens are spaced apart; and a reference transmittance cuvette is arranged between and spaced apart from the first collimator lens and the reference photodetector;

wherein the measurement sample light-source-circuit comprises a second collimator lens; a sample photodetector is arranged at a side of the second collimator lens, and the sample photodetector and the second collimator lens are spaced apart; and a sample transmittance cuvette is arranged between and spaced apart from the second collimator lens and the sample photodetector;

wherein the continuous sampling system comprises a first peristaltic pump and a second peristaltic pump; a liquid inlet end of the first peristaltic pump is communicated with the water and fertilizer storage box, and a liquid outlet end of the first peristaltic pump is communicated with a liquid inlet of the sample transmittance cuvette; a liquid inlet end of the second peristaltic pump is communicated with a reference sample pool, and a liquid outlet end of the second peristaltic pump is communicated with a liquid inlet of the reference transmittance cuvette.

2. An in-situ detection method of detecting water and fertilizer content in a crop cultivation substrate, the in-situ detection method being carried out by an in-situ detection device for detecting water and fertilizer content in the crop cultivation substrate, wherein the in-situ detection device comprises a water and fertilizer in-situ collector and a spectral analysis device; the water and fertilizer in-situ collector is pre-buried in the crop cultivation substrate and used to collect water and fertilizer in the crop cultivation substrate in real time to obtain a measurement sample; the spectral analysis device is used to emit a laser with a specific wavelength to detect and analyze content of nitrogen, phosphorus, and potassium in the measurement sample collected by the water and fertilizer in-situ collector; and a continuous sampling system for continuously transporting the measurement sample is provided between the water and fertilizer in-situ collector and the spectrum analysis device; wherein the in-situ detection method comprises:

pre-burying the water and fertilizer in-situ collector in the crop cultivation substrate;

penetrating the water and fertilizer in the crop cultivation substrate into a water and fertilizer collection box of the water and fertilizer in-situ collector through a filtration and permeation layer on the water and fertilizer collection box; and enabling the water and fertilizer to enter a water and fertilizer storage box of the water and fertilizer in-situ collector through a communicating pipe to obtain the measurement sample;

enabling the continuous sampling system to continuously transport a reference sample and the measurement sample to a measurement reference light-source-circuit and a measurement sample light-source-circuit in a multi-mode laser splitter, respectively;

enabling a laser light source of the spectrum analysis device to emit light with a specific wavelength and transmitting the light to the multi-mode laser splitter; enabling the multi-mode laser splitter to split the light into a measurement reference laser-beam and a measurement sample laser-beam; enabling the measurement reference laser-beam to be transmitted along the measurement reference light-source-circuit to a reference transmittance cuvette, so as to irradiate the reference sample; enabling the measurement sample laser-beam to be transmitted to a sample transmittance cuvette along the measurement sample light-source-circuit, so as to irradiate the measurement sample;

enabling a reference photodetector of the measurement reference light-source circuit to detect absorbance when the measurement reference laser-beam irradiates the reference sample in the reference transmittance cuvette, so as to obtain reference absorbance;

enabling a sample photodetector of the measurement sample light-source-circuit to detect absorbance when the measurement sample laser-beam irradiates the measurement sample in the sample transmittance cuvette, so as to obtain sample absorbance;

obtaining signals of both the reference absorbance and the sample absorbance; obtaining actual sample absorbance, through a formula that the sample minus the reference absorbance is the actual sample absorbance; and calculating content of corresponding nutrient elements in the measurement sample according to the actual sample absorbance;

wherein the water and fertilizer in-situ collector comprises the water and fertilizer collection box and the water and fertilizer storage box; the communicating pipe is provided between the water and fertilizer collection box and the water and fertilizer storage box; the water and fertilizer collection box is used to collect water and fertilizer in the crop cultivation substrate in real time, to obtain the measurement sample; and the measurement sample is transported into the water and fertilizer storage box through the communicating pipe;

wherein a top collection port of the water and fertilizer collection box is provided with the filtration and permeation layer for filtering soil of the crop cultivation substrate; and a float liquid-level-detection switch is arranged in the water and fertilizer storage box;

wherein the spectrum analysis device comprises the laser light source; the laser light source is connected with the multi-mode laser splitter by a quartz fiber; the multi-mode laser splitter is installed with two light source circuits; and the two light source circuits comprise the measurement reference light-source-circuit and the measurement sample light-source-circuit;

wherein the measurement reference light-source circuit comprises a first collimator lens, the reference photodetector is arranged at a side of the first collimator lens, and the reference photodetector and the first collimator lens are spaced apart; and the reference transmittance cuvette is arranged between and spaced apart from the first collimator lens and the reference photodetector;

wherein the measurement sample light-source-circuit comprises a second collimator lens, the sample photodetector is arranged at a side of the second collimator lens, and the sample photodetector and the second collimator lens are spaced apart; and the sample transmittance cuvette is arranged between and spaced apart from the second collimator lens and the sample photodetector;

wherein the continuous sampling system comprises a first peristaltic pump and a second peristaltic pump; a liquid inlet end of the first peristaltic pump is communicated with the water and fertilizer storage box, and a liquid outlet end of the first peristaltic pump is communicated with a liquid inlet of the sample transmittance cuvette; a liquid inlet end of the second peristaltic pump is communicated with a reference sample pool, and a liquid outlet end of the second peristaltic pump is communicated with a liquid inlet of the reference transmittance cuvette.

3. The in-situ detection method of water and fertilizer content in the crop cultivation substrate according to claim 2, wherein the step of enabling a laser light source, the laser light source comprises a laser light source for detecting nitrogen, a laser light source for detecting phosphorus, and a laser light source for detecting potassium; a wavelength of the laser light source for detecting nitrogen is 217 nm; a wavelength of the laser light source for detecting phosphor is 490 nm; and a wavelength of the laser light source for detecting potassium is 440 nm.

\* \* \* \* \*